US008282587B2

(12) United States Patent
McSpadden et al.

(10) Patent No.: US 8,282,587 B2
(45) **Date of Patent: *Oct. 9, 2012**

(54) METHOD OF AND SYSTEM FOR JOINT THERAPY AND STABILIZATION

(75) Inventors: Sam K. McSpadden, Austin, TX (US); Tony Quisenberry, Highland Village, TX (US)

(73) Assignee: ThermoTek, Inc., Flower Mound, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,247

(22) Filed: Sep. 21, 2011

(65) Prior Publication Data

US 2012/0010545 A1 Jan. 12, 2012

Related U.S. Application Data

(63) Continuation of application No. 12/485,840, filed on Jun. 16, 2009, now Pat. No. 8,043,242.

(60) Provisional application No. 61/061,888, filed on Jun. 16, 2008.

(51) Int. Cl.
*A61F 5/00* (2006.01)

(52) U.S. Cl. .................. 602/13; 602/2; 602/16; 602/23; 602/26

(58) Field of Classification Search .................. 602/2, 5, 602/16, 20, 23, 26, 27, 13; 128/882
See application file for complete search history.

(56) References Cited

U.S. PATENT DOCUMENTS 3,913,302 A 10/1975 Centers
4,115,902 A 9/1978 Taylor
4,130,115 A 12/1978 Taylor
4,198,834 A 4/1980 Reid et al.
4,287,885 A 9/1981 Applegate
4,494,534 A 1/1985 Hutson
4,585,003 A 4/1986 Meistrell
4,628,916 A 12/1986 Lerman et al.
4,700,406 A 10/1987 Meistrell
4,706,673 A 11/1987 Meistrell
4,729,370 A 3/1988 Kallassy
4,805,606 A 2/1989 McDavid, III
4,805,620 A 2/1989 Meistrell
4,841,957 A 6/1989 Wooten et al.
4,856,501 A 8/1989 Castillo et al.
4,873,967 A 10/1989 Sutherland
4,941,462 A * 7/1990 Lindberg ........................ 602/16
4,986,264 A 1/1991 Miller
5,024,216 A 6/1991 Shiono
5,050,620 A 9/1991 Cooper
5,086,761 A 2/1992 Ingram
5,261,871 A 11/1993 Greenfield
5,267,946 A 12/1993 Singer et al.
5,277,697 A 1/1994 France et al.
5,314,455 A * 5/1994 Johnson et al. ............... 607/104
5,433,699 A 7/1995 Smith et al.
5,455,969 A 10/1995 Pratson et al.
5,554,104 A 9/1996 Grim
(Continued)

*Primary Examiner* — Michael A. Brown
(74) *Attorney, Agent, or Firm* — Winstead PC

(57) ABSTRACT

A joint therapy system and method is shown for proving thermal therapy and joint stability in dual modes of operation. In some embodiments, a treatment system is shown utilizing an orthopedic support for supporting a joint region and having one or more of temperature control capabilities, compression capabilities, and bracing capabilities that may, for example, be used to reduce recover time, limit edema, and protect joints from improper movement while healing from orthopedic surgeries.

15 Claims, 12 Drawing Sheets

U.S. PATENT DOCUMENTS 5,562,605 A 10/1996 Taylor et al.
5,624,389 A 4/1997 Zepf et al.
5,658,243 A 8/1997 Miller et al.
5,741,220 A * 4/1998 Brink .............................. 602/14
5,759,167 A * 6/1998 Shields et al. .................. 602/26
5,782,785 A 7/1998 Herzberg
5,792,084 A 8/1998 Wilson et al.
5,795,312 A 8/1998 Dye
5,807,298 A 9/1998 Palumbo
5,810,752 A 9/1998 Grifka et al.
5,857,988 A 1/1999 Shirley
5,865,776 A 2/1999 Springs
5,873,848 A 2/1999 Fulkerson
5,921,946 A 7/1999 Tillinghast et al.
6,066,110 A 5/2000 Nauert
6,117,164 A * 9/2000 Gildersleeve et al. ........ 607/108
6,120,472 A 9/2000 Singer, Jr.
6,135,974 A 10/2000 Matz
6,142,965 A 11/2000 Mathewson
6,190,344 B1 2/2001 Bobroff
6,203,511 B1 3/2001 Johnson et al.
6,287,269 B1 9/2001 Osti et al.
7,060,045 B2 6/2006 Mason et al.
7,217,249 B2 5/2007 Scott
8,043,242 B2 * 10/2011 McSpadden et al. ........... 602/13
2002/0077574 A1 6/2002 Gildersleeve et al.
2003/0060845 A1 3/2003 Gardon-Mollard
2005/0020951 A1 * 1/2005 Gaylord et al. ................. 602/26
2007/0197947 A1 8/2007 Scott
2008/0300524 A1 12/2008 Scott
2009/0156973 A1 6/2009 Scott

* cited by examiner

METHOD OF AND SYSTEM FOR JOINT THERAPY AND STABILIZATION

CROSS-REFERENCE TO RELATED APPLICATIONS

This application is a continuation of and incorporates by reference the entire disclosure of U.S. patent application Ser. No. 12/485,840, filed Jun. 16, 2009 now U.S. Pat. No. 8,043,242. U.S. patent application Ser. No. 12/485,840 claims priority from and incorporates by reference the entire disclosure of U.S. Provisional Patent Application No. 61/061,888, filed Jun. 16, 2008.

BACKGROUND

1. Technical Field

The present invention relates to a method of and system for joint therapy and stabilization and, more particularly, but not by way of limitation, to a treatment system utilizing an orthopedic support for supporting a joint region such as, for example, a knee and having one or more of temperature control capabilities, compression capabilities, and bracing capabilities.

2. History of Related Art

It is common in the sports medicine industry to utilize orthopedic supports for various body parts subject to injury. The most common support areas include the knees, elbows, wrists, shoulders, backs, and ankles. Often injuries to these areas of the body can be treated by the utilization of the appropriate orthopedic support. In the event of surgery, rehabilitation is sometimes augmented by the utilization of such supports.

The design of orthopedic supports has changed considerably over the past two decades. The types of material used as well as the fastening and hinging mechanisms associated with orthopedic supports have been the subject of considerable study and improvement. U.S. Pat. No. 4,986,264 to Miller, teaches a knee brace having an interior tibial shell and an interior femoral shell which are closely configured to the shape of the lower leg and thigh respectively and which are joined by a frame in the form of a pair of polycentric hinge joints. U.S. Pat. No. 4,856,501 to Castill et. al. teaches a knee brace having adjustable width frame pivoted to cuffs. The brace as set forth therein includes first and second frame members disposed on opposite sides of the joint to be supported, and first and second hinge members disposed substantially adjacent to the joint and connected to the frame members to pivot the frame members about the joint.

There is a need in the art for a treatment system utilizing an orthopedic support for a joint region that provides a new level of flexibility and customizability along with one or more of temperature control capabilities, compression capabilities, and bracing capabilities that may, for example, be used to reduce recover time, limit edema, and protect knees from improper movement while healing from orthopedic surgeries.

SUMMARY

In various embodiments, a system for joint therapy and stabilization is shown, the system including an expandable orthopedic device operable for dual modes of use, a first mode being thermal therapy and a second mode being joint stabilization; a thermal therapy wrap configured to be removably attached to an inside surface of the expandable orthopedic device during the first mode of use; the expandable orthopedic device comprising a first portion and a second portion; wherein circumferences of both the first and second portions are adjustable to accommodate the thermal therapy wrap during the first mode of use and to provide joint stabilization in the second mode; wherein the expandable orthopedic device comprises a first joint stabilization member adjustably attached on an outside surface of the expandable orthopedic device and a second joint stabilization member adjustably attached on the outside surface of the expandable orthopedic device opposite the first joint stabilization member; and wherein the first and second joint stabilization members are adjustable to provide joint stabilization in both the first and second modes of use.

In some embodiments, the expandable orthopedic device may include a patella opening. In some embodiments, the inside surface of the expandable orthopedic device around a circumferential edge of the patella opening may be constructed of hook and pile portions to engage and facilitate adjustability of the thermal therapy wrap. In some embodiments, the thermal therapy wrap may include an inflatable compression bladder; and a plurality of fluid tubes operable to be connected to a fluid pump having thermal control and compression capabilities. In some embodiments, the system may include a support buttress configured to be removably attached to the inside surface of the expandable orthopedic device during the second mode of use. In some embodiments, the expandable orthopedic device may be operable to interchangeably receive the buttress, the buttress being operable to be adjustably positioned on an inside surface of the expandable orthopedic device around a circumferential edge of the patella opening. In some embodiments, the buttress may be horse-shoe like in shape and may be positioned in a medial and/or a lateral direction relative to a user's patella for knee stabilization.

In some embodiments, a method for providing orthopedic therapy is shown, the method including providing an expandable orthopedic device having an upper fastener assembly comprising a first strap and a lower fastener assembly comprising a second strap; attaching a thermal therapy wrap on an inside surface of the expandable orthopedic device, the thermal therapy wrap being operable to provide hot and/or cold therapy; wrapping the expandable orthopedic device incorporating the thermal therapy wrap around a leg portion of a user and securing the expandable orthopedic device therearound; positioning first and second joint stabilization members on opposite sides of the leg portion of the user to provide joint stabilization; providing hot and/or cold therapy to the user; removing the thermal therapy wrap from the inside surface of the expandable orthopedic device; attaching a buttress on an inside surface of the expandable orthopedic device; wrapping the expandable orthopedic device incorporating the thermal therapy wrap around the leg portion of the user and securing the expandable orthopedic device therearound; and adjusting the first and second joint stabilization members to provide joint stabilization.

In some embodiments, a system for joint therapy and stabilization is shown, the system including an expandable orthopedic device adapted to circumscribe portions of a user above and below a joint of the user and operable for dual modes of use, a first mode being thermal therapy and a second mode being joint stabilization; a thermal therapy wrap configured to be removably attached to an inside surface of the expandable orthopedic device during the first mode of use; first and second joint stabilization members each having first and second portions rotatable about a point of rotation; wherein circumferences of the expandable orthopedic device above and below the joint are each adjustable to accommodate the thermal therapy wrap during the first mode of use and to provide joint stabilization in the second mode; wherein the first and second joint stabilization members are each adjustably attached to the expandable orthopedic device; and wherein the first and second joint stabilization members are adjustably disposed so that the point of rotation of each of the first and second joint stabilization members is aligned with a point of rotation of the joint in both the first and second modes of use.

The above summary of the invention is not intended to represent each embodiment or every aspect of the present invention.

BRIEF DESCRIPTION OF THE DRAWINGS

A more complete understanding of the system of the present invention may be obtained by reference to the following Detailed Description when taken in conjunction with the accompanying Drawings wherein.

DETAILED DESCRIPTION OF THE INVENTION

Various embodiments of the present invention will now be described more fully with reference to the accompanying drawings. The invention may, however, be embodied in many different forms and should not be construed as limited to the embodiments set forth herein; rather, the embodiments are provided so that this disclosure will be thorough and complete, and will fully convey the scope of the invention to those skilled in the art.

Referring now to FIGS. 1-9, an embodiment of a joint therapy and stabilization system 100 will be described in detail. In a typical embodiment, the joint therapy and stabilization system 100 may be utilized in areas of need such as, for example, a limb region of a user. The limb region may be, for example, a knee region, an ankle region, an elbow region, a wrist region, a shoulder region, a back region, or the like of the user. For illustrative purposes, various embodiments shown and described herein are shown and described relative to a knee joint of a user, but various embodiments of the joint therapy and stabilization system 100 may be utilized to provide joint therapy and stabilization for various other joints and/or regions of a user.

In the embodiment shown, the joint therapy and stabilization system 100 may include an expandable orthopedic device 10, a support buttress 116, and a thermal therapy wrap 106. In a typical embodiment, the therapy and stabilization system 100 may be used, for example, to reduce recovery time, limit edema, and protect joints from improper movement while healing from orthopedic surgeries by having temperature control capabilities, compression capabilities, and bracing capabilities details of which will be described below.

Figure 1:
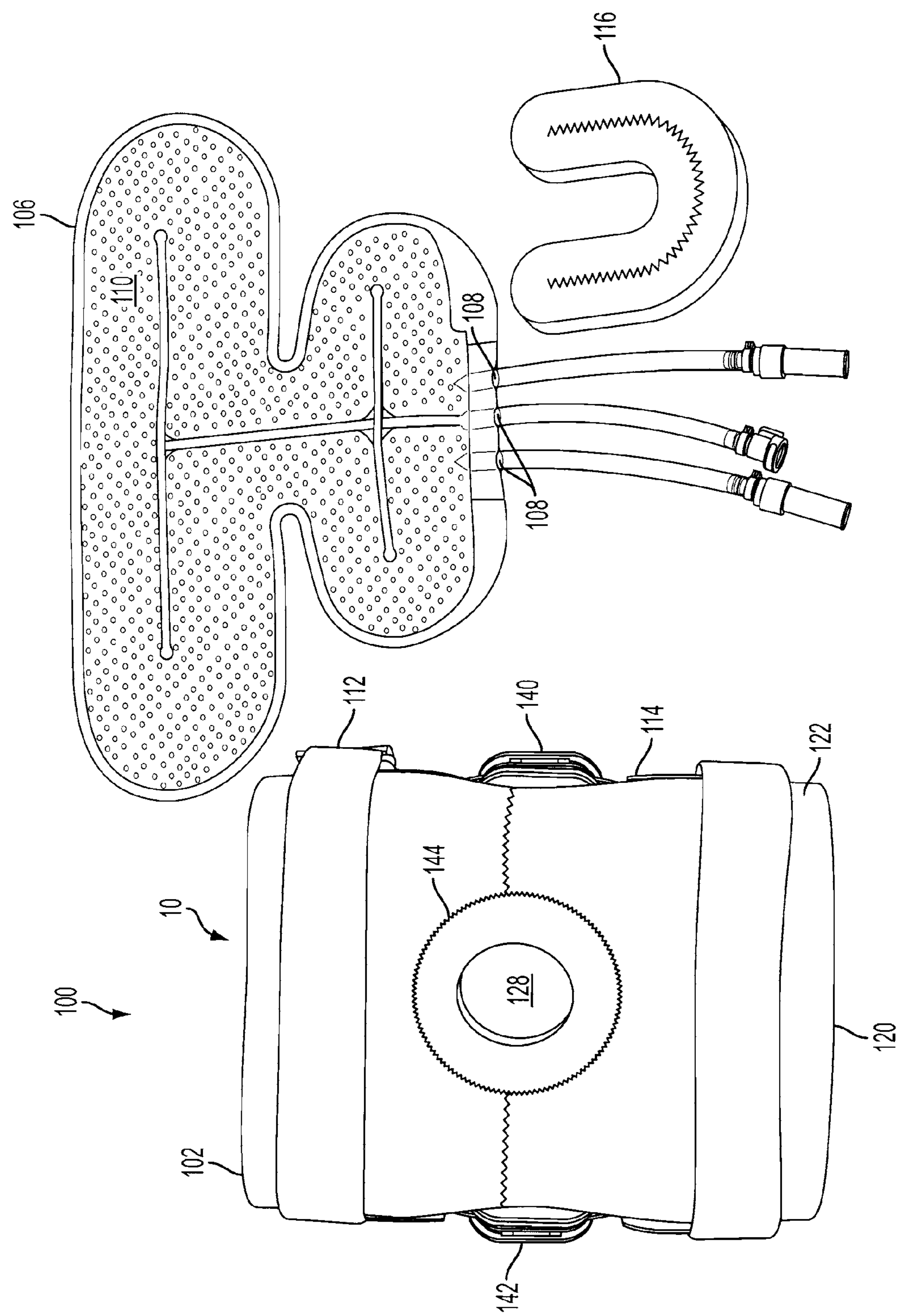
FIG. 1 is a front view of elements of an embodiment of a therapy system.

The expandable orthopedic device 10 comprises an upper fastener assembly having a strap 112 and a lower fastener assembly having a strap 114. While only two straps are shown in FIG. 1, it will be understood to one of ordinary skill in the art that various embodiments may include any number of straps. The expandable orthopedic device 10 may be constructed using any natural or synthetic material, including both inelastic and elastic materials, having sufficient flexibility and resiliency to enable the expandable orthopedic device 10 to anatomically conform to the body member to which it is applied. For example, the expandable orthopedic device 10 may be formed of, for example, two-sided nylon Neoprene, which provides durability and elasticity. The two-sided nylon Neoprene allows the expandable orthopedic device 10 to be easily wrapped around a user leg and more particularly the knee area. According to an exemplary embodiment, the two-sided nylon Neoprene has an approximate thickness between ⅛ to 3/16 inch. The outside, comprising a front side 120 and a back side 122, is constructed of UBL, which is standard and well known in the art. The body of straps 112 and 114, with the exception of fasteners 126 and 130 (illustrated in FIG. 4) may be constructed with hook and pile portions to facilitate adjustability and ease of use by the user.

The expandable orthopedic device 10 may include a large patella opening 128. Upper and lower outer straps 112 and 114 comprise fastener portions 126 and 130 extending from distal ends. Once the expandable orthopedic device 10 is placed onto a user's joint, for example, a knee area, an upper inner strap 132 and a lower inner strap 134 wrap around a back portion of the knee. For example, the upper inner strap 132 is operable to wrap around a lower portion of a thigh region and the lower inner strap 134 is operable to wrap around an upper calf portion of a user's leg. The upper and lower outer straps 112 and 114 are then wrapped over the upper and lower inner straps 132 and 134, respectively, and fastener portions 126 and 130 are attached thereto.

According to exemplary embodiments, the fastener portions 126 and 130 may be constructed of hook and pile portions while the upper and lower inner straps 132, 134 may contain loop material so that they may be secured against each other and to facilitate adjustability and ease of use by the user. The upper and lower outer straps 112 and 114, in conjunction with the upper and lower inner straps 132 and 134, may be of sufficient length to encompass the thigh and calf regions at least once. Additionally, a space between the upper and lower outer straps 112 and 114 and a space between the upper and lower inner straps 132 and 134 provides for a popliteal opening 202 (illustrated in FIG. 2B) when expandable orthopedic device 10 is secured around a user's knee. It will be appreciated that compression may be adjusted to a desired level by increasing or decreasing the tightness of the upper and lower outer straps 112 and 114 around the thigh and calf regions.

A first joint stabilization member 140 is distinctly placed along an outside surface of the expandable orthopedic device 10. According to an exemplary embodiment, the joint stabilization member 140 may be, for example, a polycentric (double axis) hinge, a single axis hinge, a complex hinge, or a spiral stay. A second joint stabilization member 142 is disposed on an outside surface of the expandable orthopedic device 10 and opposite the first joint stabilization member 140, and is positioned in such a way to balance the support about the joint. Stitching 144 is shown around the patella opening 128. This stitching is shown for purposes of illustration only, and other stitching embodiments may be incorporated herein.

The therapy and stabilization system 100 further includes a thermal therapy wrap 106. In a typical embodiment, the thermal therapy wrap 106 is substantially butterfly shaped; however, in other embodiments of the invention, the thermal therapy wrap 106 may be other shapes such as, for example, square, round, and the like. In a typical embodiment, the thermal therapy wrap 106 includes an inflatable compression bladder 110 contained in, for example, a textile covering such as, for example, nylon. The thermal therapy wrap 106 further includes a plurality of fluid tubes 108 located beneath the inflatable compression bladder 110. In a typical embodiment, the fluid tubes 108 may be, for example, a fluid flow temperature bladder. The fluid flow temperature bladder and the inflatable compression bladder 110 may be connected via a flexible hose to a precision fluid pump having thermal control and compression capabilities.

The thermal therapy wrap 106 is operable to be placed on an inside surface of the expandable orthopedic device 10. In a typical embodiment, the inside surface of the expandable orthopedic device 10 may be constructed with hook and pile portions to engage the thermal therapy wrap 106. The thermal therapy wrap 106 may be adjustably positioned on the inside surface of the expandable orthopedic device 10 and is operable to reduce recovery time and limit edema by having temperature control capabilities and compression capabilities. In a typical embodiment, the thermal therapy wrap 106 incorporated within the expandable orthopedic device 10 is operable to provide hot and/or cold therapy resulting in faster relief. Furthermore, the combination of the thermal therapy wrap 106 and the expandable orthopedic device 10 is operable to, for example, accelerate post surgery healing, post workout fatigue, treat swelling, treat inflammation, treat sprains, treat joint and muscle pain, treat muscle spasms, and treat any other related injuries.

The joint therapy and stabilization system 100 further includes a patella support buttress 116. In a typical embodiment, the buttress 116 may be constructed with hook and pile portions to facilitate adjustability. The buttress 116 includes a front side 150 and a back side 152 (illustrated in FIGS. 3A-3B). According to an exemplary embodiment, the front side 150 is made of a material that has grip characteristics and prevents slippage when placed against human skin such as, for example, shark-skin. The back side 152 of the buttress 116 may be constructed with hook and pile portions to facilitate adjustability and ease of use by the user. The buttress 116 is operable to be placed on an inside surface of the expandable orthopedic device 10 around a location on a circumferential edge of the patella opening 128. In a typical embodiment, the inside surface of the expandable orthopedic device 10 around the circumferential edge of the patella opening 128 may be constructed with hook and pile portions to engage the buttress 116 in order to facilitate adjustability of the buttress 116. The buttress 116 may be adjustably positioned on the inside surface of the expandable orthopedic device 10 around a location on the circumferential edge of the patella opening 128 to provide knee stabilization. According to an exemplary embodiment, the buttress 116 can be positioned in a medial or lateral direction relative to the user's patella.

Figure 2A:
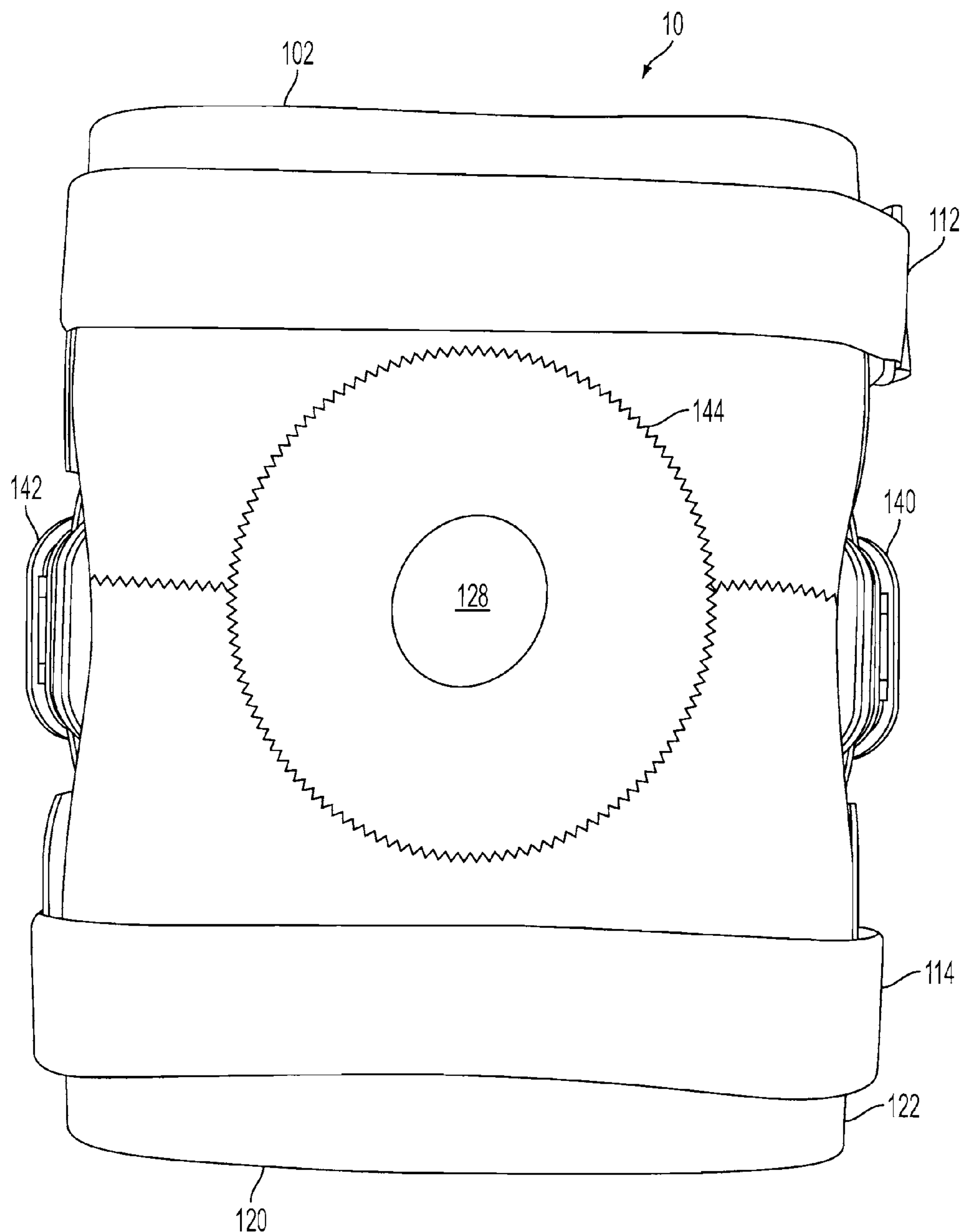
FIG. 2A is a front view of an exemplary configuration of an embodiment of a therapy system.
Figure 2B:
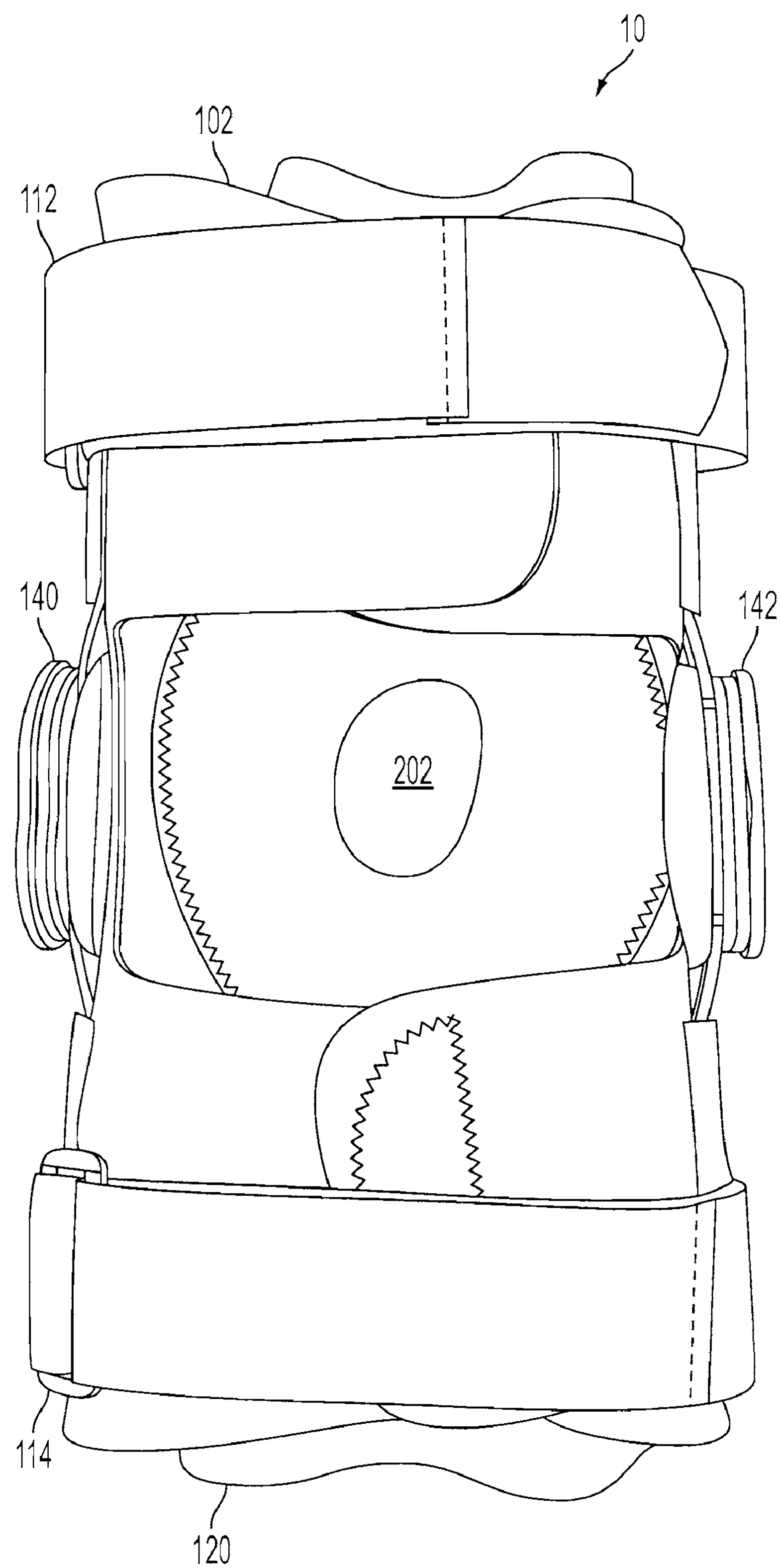
FIG. 2B is a back view of the therapy system of FIG. 2A.

FIGS. 2A-2B illustrate front and back views, respectively, of a expandable orthopedic device 10 according to an exemplary embodiment. The expandable orthopedic device 10 further includes a popliteal opening 202 opposite the patella opening 128 for added comfort. It is important to note that FIGS. 1-9 and the description herein are directed to a therapy and stabilization system 100 utilizing a universal expandable orthopedic device 10 having one or more of temperature control capabilities, compression capabilities, and bracing capabilities and can be worn interchangeably on the left and the right knee of the user.

Figure 3A:
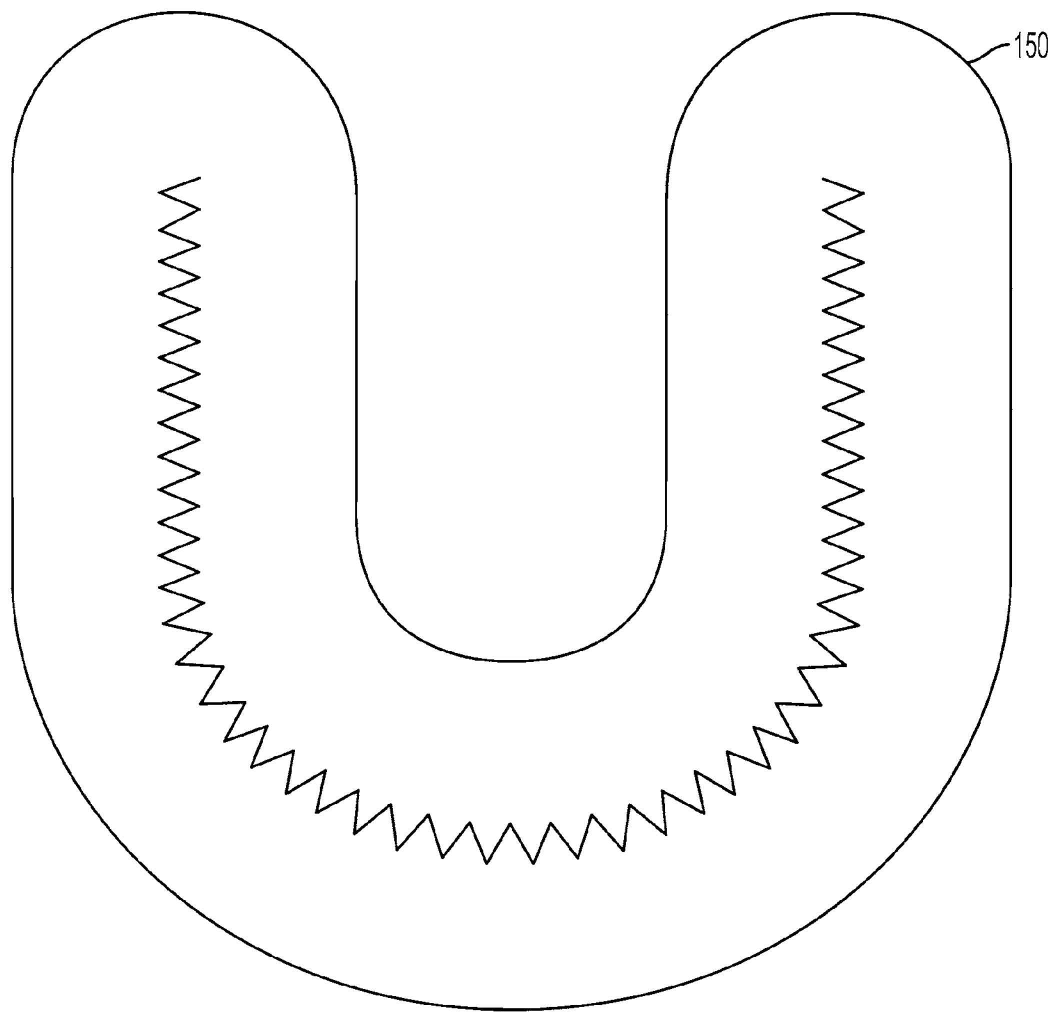
FIG. 3A is a front view of a buttress of the therapy system of FIG. 1.
Figure 3B:
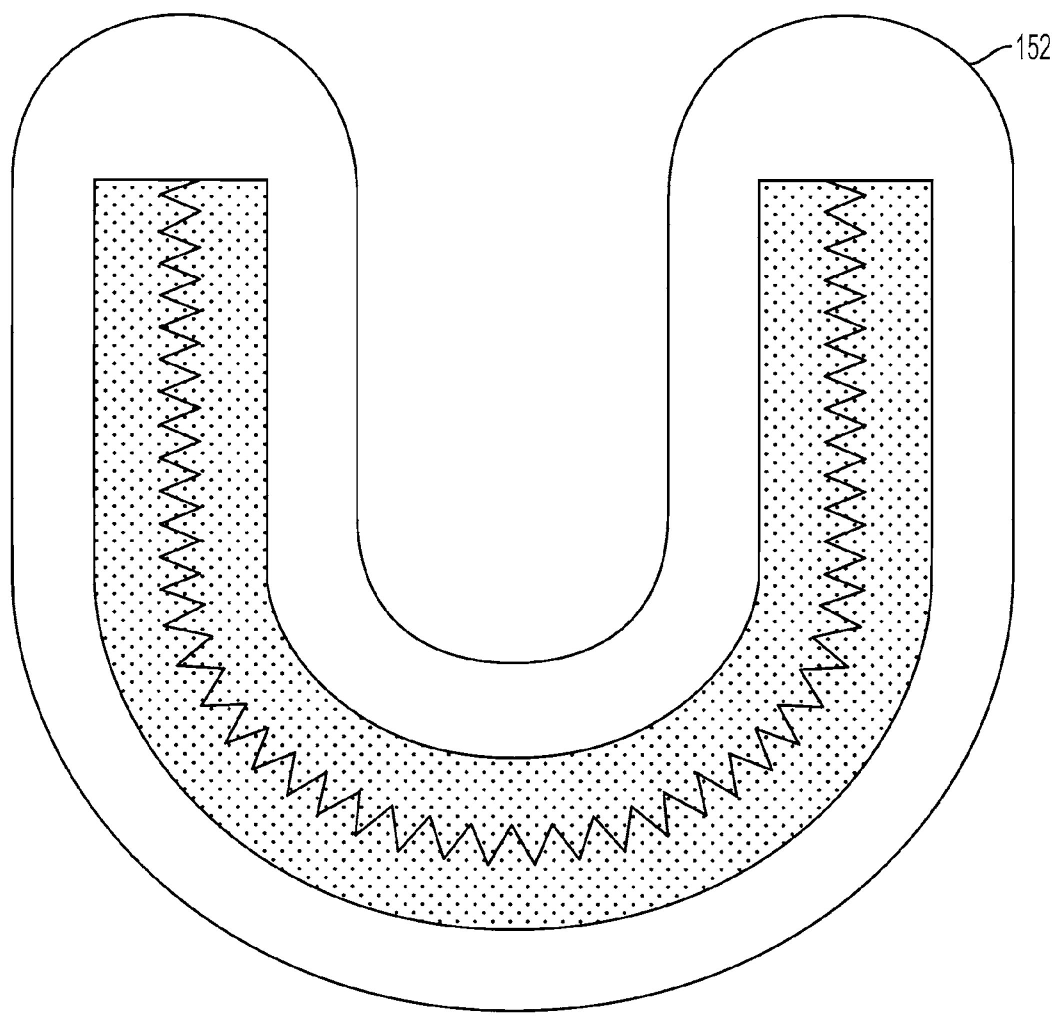
FIG. 3B is a back view of the buttress of FIG. 3A.

FIGS. 3A-3B illustrate front and back views of a buttress 116 of the therapy and stabilization system 100 in accordance with one aspect of an embodiment. The buttress 116 includes a front side 150 and a back side 152. According to an exemplary embodiment, the front side 150 is made of a material that has grip characteristics and prevents slippage when placed against human skin. The back side 152 of the buttress 116 may be constructed with hook and pile portions to facilitate adjustability and ease of use by the user. The buttress 116 is operable to be placed on an inside surface of the expandable orthopedic device 10 around a location on a circumferential edge of the patella opening 128. According to an exemplary embodiment, the buttress 116 is horse-shoe like in shape. However, the buttress 116 may be of other shapes such that the buttress 116 can be placed on an inside surface of the expandable orthopedic device 10 around a location on a circumferential edge of the patella opening 128 to provide a desired pressure and properly align the user's patella for knee stabilization.

Figure 4:
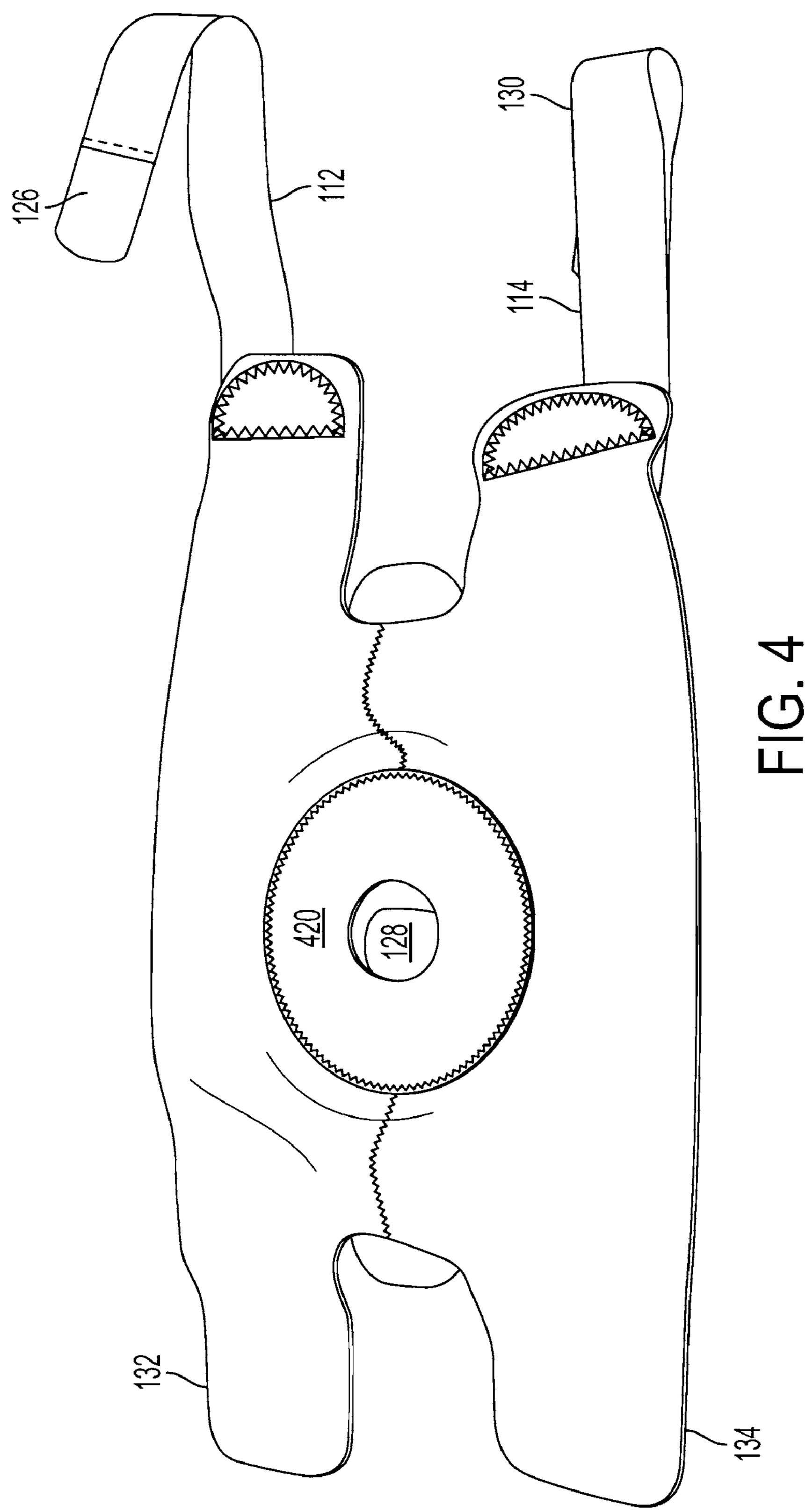
FIG. 4 is a view of an inside surface an expandable orthopedic device in an unwrapped position.

FIG. 4 is an illustration of an inside view of the expandable orthopedic device 10 in accordance with an embodiment. The expandable orthopedic device 10 includes a large patella opening 128. According to an exemplary embodiment, the inside surface of the expandable orthopedic device 10 around the circumferential edge of the patella opening 128 may be constructed with hook and pile portions 420 to engage and facilitate adjustability of the buttress 116 and the thermal therapy wrap 106 for injury prevention and/or recovery healing treatment after surgeries.

Figure 5A:
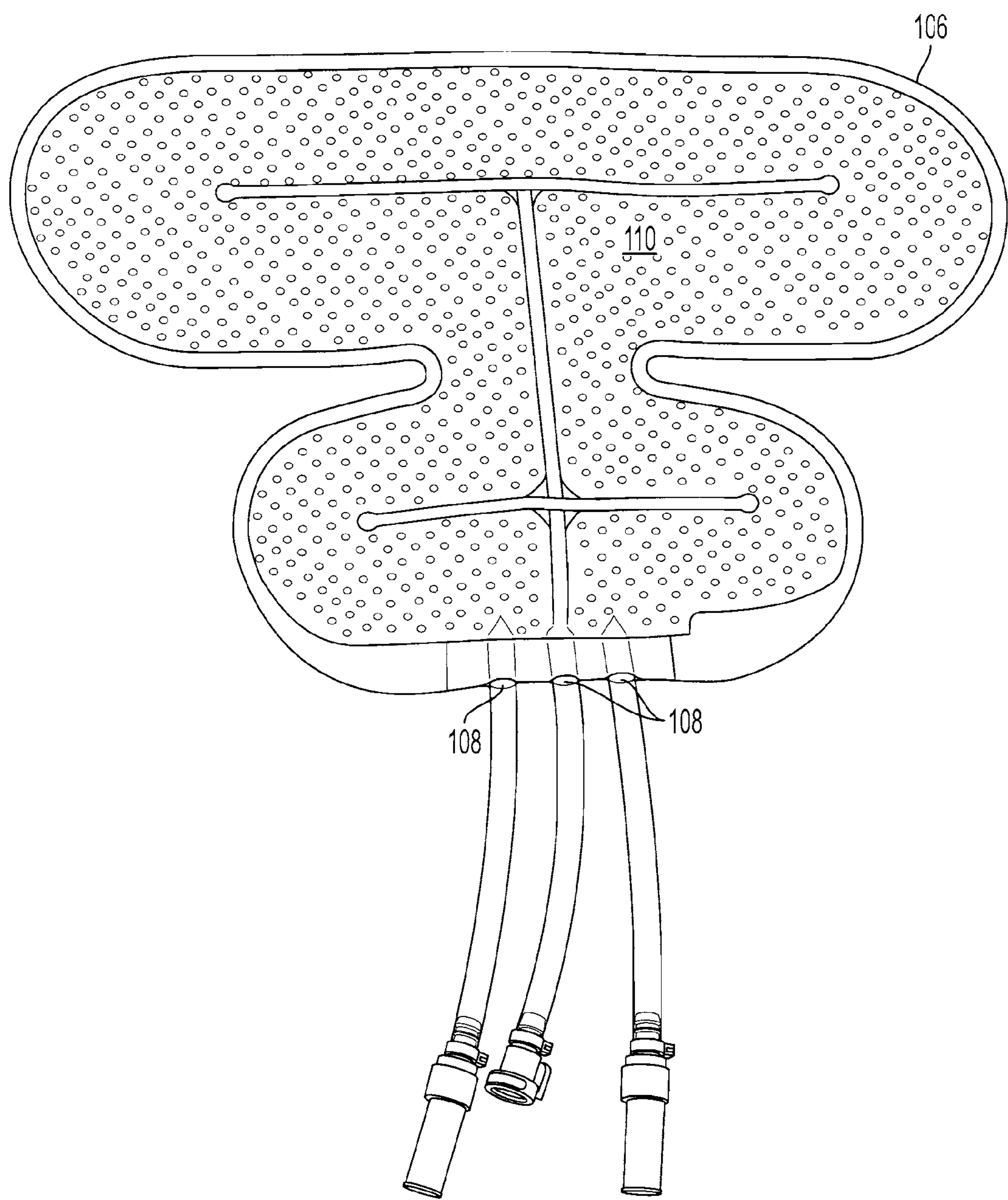
FIG. 5A is a front view of a thermal therapy wrap of the therapy system of FIG. 1.
Figure 5B:
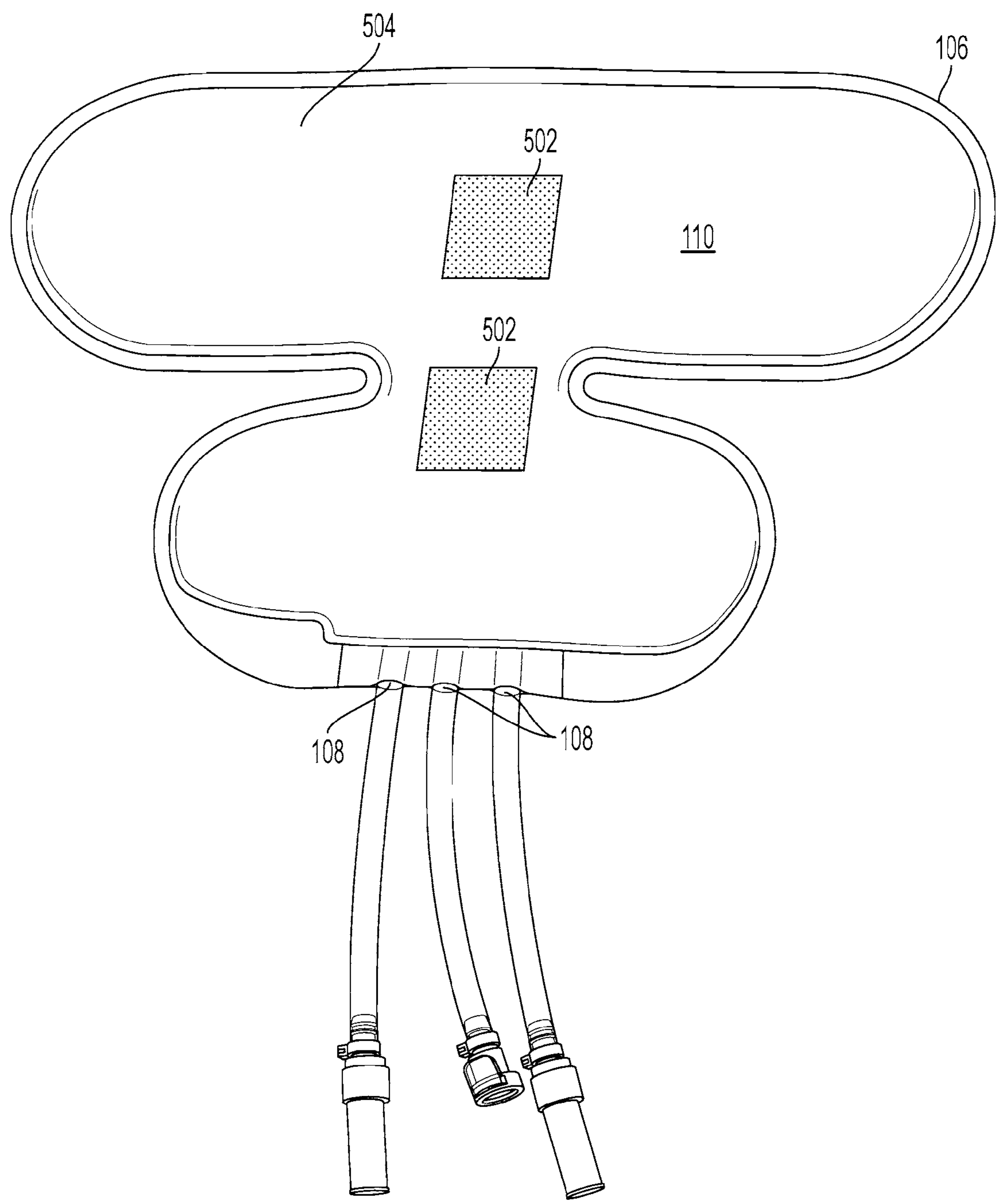
FIG. 5B is a back view of the thermal therapy wrap of FIG. 5A.

FIGS. 5A-5B illustrate front and back views of a thermal therapy wrap 106 in accordance with an embodiment. In a typical embodiment, the thermal therapy wrap 106 is substantially butterfly shaped; however, in other embodiments of the invention, the thermal therapy wrap 106 may be other shapes such as, for example, square, round, and the like. In a typical embodiment, the thermal therapy wrap 106 includes an inflatable compression bladder 110 contained in, for example, a textile covering such as, for example, nylon. The thermal therapy wrap 106 further includes a plurality of fluid tubes 108 located beneath an inflatable compression bladder 110. In a typical embodiment, the fluid tubes 108 may be, for example, a fluid flow temperature bladder. The fluid flow temperature bladder and the inflatable compression bladder 110 may be connected to a precision fluid pump having thermal control and a compression pump by a flexible hose.

The thermal therapy wrap 106 is operable to be placed on an inside surface of the expandable orthopedic device 10. In a typical embodiment, the inside surface of the expandable orthopedic device 10 may be constructed with hook and pile portions to engage the hook and pile portions 502 on a back surface 504 of the thermal therapy wrap 106. The thermal therapy wrap 106 may be adjustably positioned on the inside surface of the expandable orthopedic device 10 may be used to reduce recover time, limit edema, and protect knees from improper movement while healing from orthopedic surgeries by having temperature control capabilities and compression capabilities. In a typical embodiment, the thermal therapy wrap 106 incorporated within the expandable orthopedic device 10 provides hot and/or cold therapy resulting in faster relief. Furthermore, the combination of the thermal therapy wrap 106 and the expandable orthopedic device 10 is operable to, for example, accelerate post surgery healing, post workout fatigue, treat swelling, treat inflammation, treat sprains, treat joint and muscle pain, treat muscle spasms, and treat any other related injuries.

Figure 6:
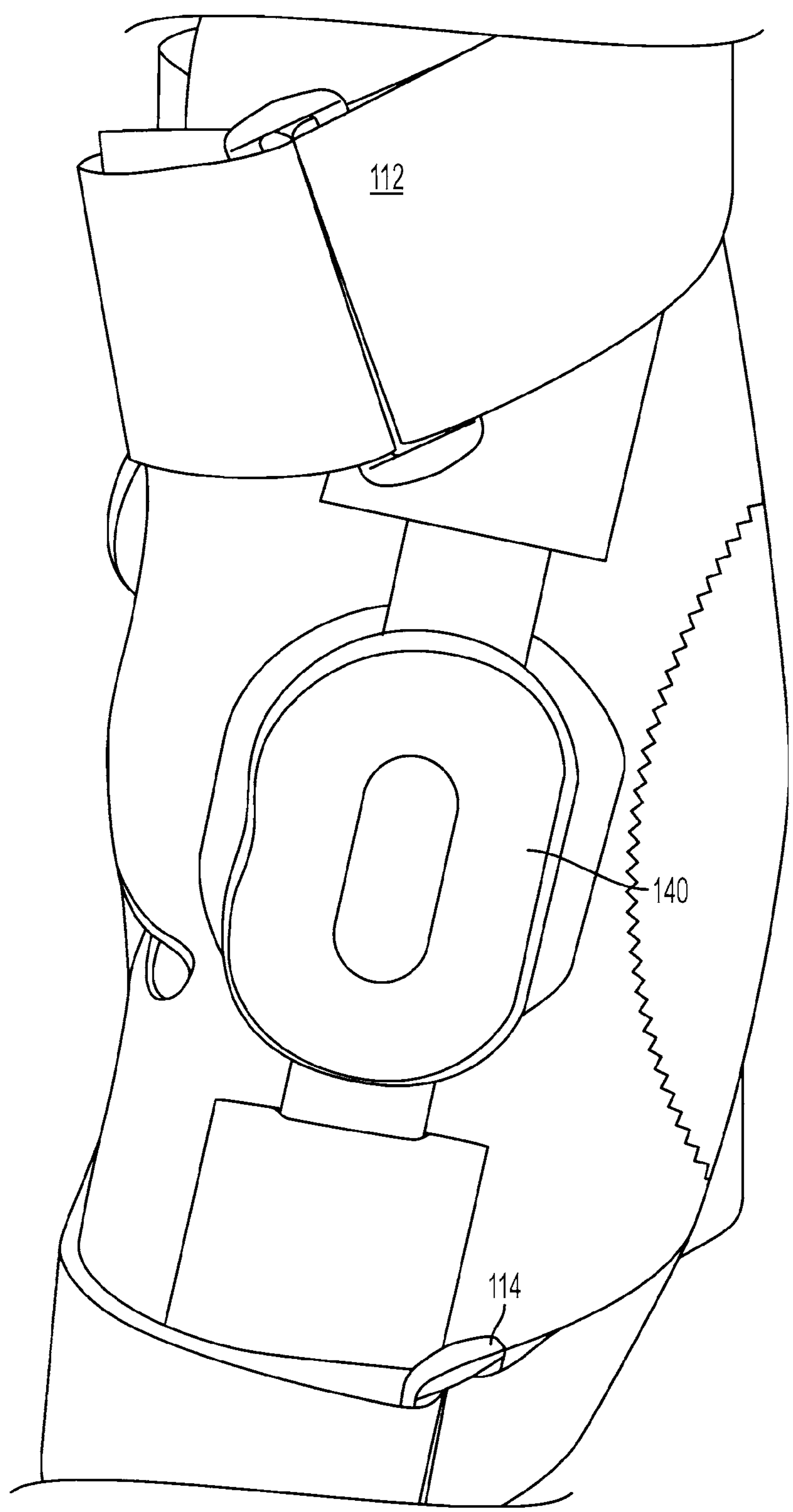
FIG. 6 is a side view of the expandable orthopedic device of FIG. 4 in a wrapped position.

FIG. 6 is a side view of the expandable orthopedic device 10 in accordance with an embodiment. In the embodiment shown, the expandable orthopedic device 10 is shown having joint stabilization member 140 disposed on an outside surface thereof. Oftentimes, the joint stabilization member 140 has a point of rotation about which first and second portions thereof rotate. Oftentimes, the joint stabilization member may need to be disposed in a particular orientation and in a particular position relative to the joint of a user so that the point of rotation of the joint stabilization member 140 aligns with the point of rotation of the joint in order to both allow joint rotation while at the same time providing joint stabilization against undesired joint movements. As described above, the expandable orthopedic device 10 may be utilized in conjunction with a thermal therapy wrap 106 in a first mode for thermal therapy and without the thermal therapy wrap 106 in a second mode for joint stabilization. In the first mode, to accommodate the thermal therapy wrap 106, the circumferences of upper and lower portions of the expandable orthopedic device 10 will be larger than the circumferences of the upper and lower portions in the second mode. In order to allow joint movement and provide joint stabilization, both the upper and lower portions of the joint stabilization member 140 will need to be adjusted, either forward or backward. In various embodiments, the joint stabilization members 140 and 142 are removably attached to the expandable orthopedic device 10 via hook and pile portions to that the upper and lower portions of the joint stabilization members can be adjustably positioned relative to the joint of a user in both the first and second modes of operation.

Figure 7A:
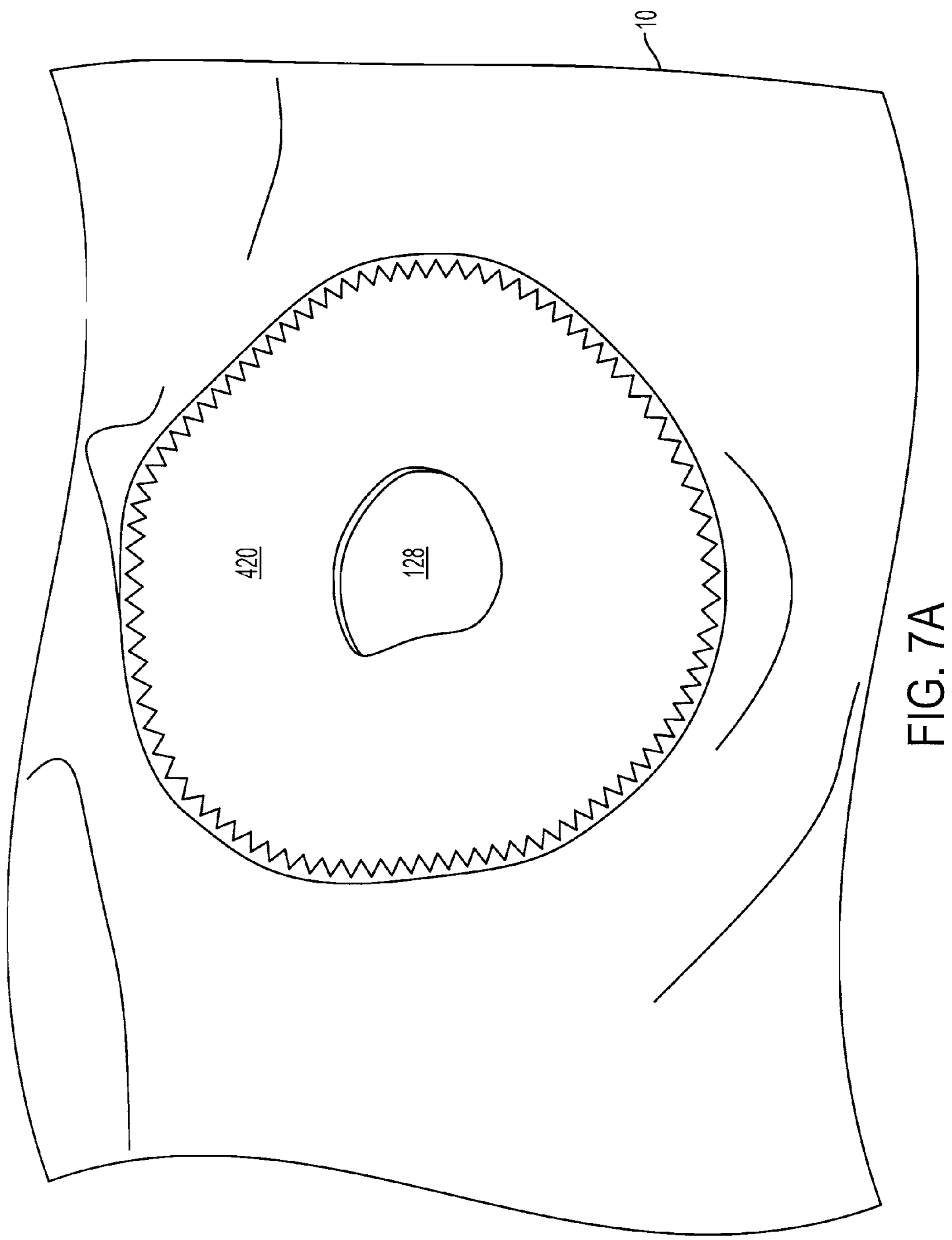
FIG. 7A is an illustration of a close up view of a patella opening of an expandable orthopedic device.

FIG. 7A is an illustration of a close-up view of a patella opening 128 of the expandable orthopedic device 10 in accordance with an embodiment. The expandable orthopedic device 10 includes a large patella opening 128. According to an exemplary embodiment, the inside surface of the expandable orthopedic device 10 around the circumferential edge of the patella opening 128 may be constructed with hook and pile portions 420 to engage and facilitate adjustability of the buttress 116 and the thermal therapy wrap 106.

In a typical embodiment, the inside surface of the expandable orthopedic device 10 may be constructed with hook and pile portions to engage the hook and pile portions 502 on a back surface 504 of the thermal therapy wrap 106. The thermal therapy wrap 106 may be adjustably positioned on the inside surface of the expandable orthopedic device 10 and is operable to reduce recover time, limit edema, and protect the knees from improper movement while healing from orthopedic surgeries. In a typical embodiment, the thermal therapy wrap 106 incorporated within the expandable orthopedic device 10 and provides hot and/or cold therapy resulting in faster relief. Furthermore, the combination of the thermal therapy wrap 106 and the expandable orthopedic device 10 is operable to, for example, accelerate post surgery healing, post workout fatigue, treat swelling, treat inflammation, treat sprains, treat joint and muscle pain, treat muscle spasms, and treat any other related injuries.

Next, after the hot and/or cold therapy is complete, the thermal therapy wrap 106 is removed and replaced with the buttress 116. In a typical embodiment, the buttress 116 is operable to be placed on an inside surface of the expandable orthopedic device 10 around a location on a circumferential edge of the patella opening 128. The buttress 116 may be adjustably positioned on the inside surface of the expandable orthopedic device 10 around a location on the circumferential edge of the patella opening 128 to provide a desired pressure and properly align a user's patella for knee stabilization.

Figure 7B:
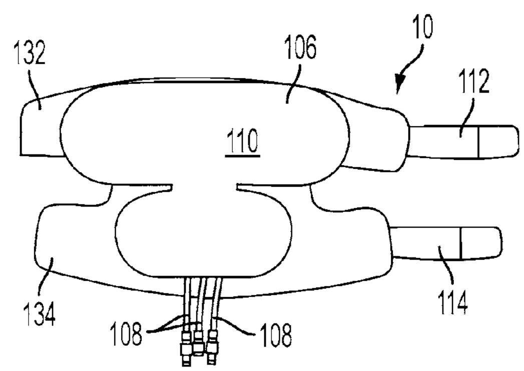
FIG. 7B is a perspective view of a thermal therapy wrap placed on an expandable orthopedic device in an unwrapped position.
Figure 7C:
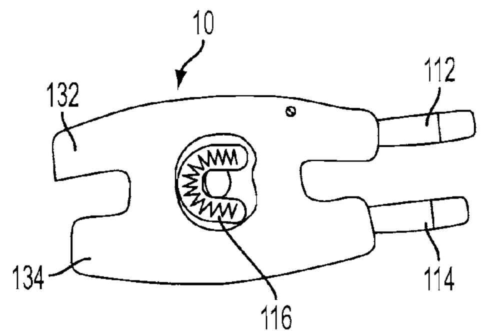
FIG. 7C is a perspective view of a buttress placed on a expandable orthopedic device in an unwrapped position.

FIGS. 7B-7C illustrate a perspective view of a thermal therapy wrap 106 and a buttress 116, respectively, placed on a expandable orthopedic device 10 in accordance with an embodiment. Details of the thermal therapy wrap 106 and the buttress 116 placed on the expandable orthopedic device 10 have been disclosed above.

Figure 8A:
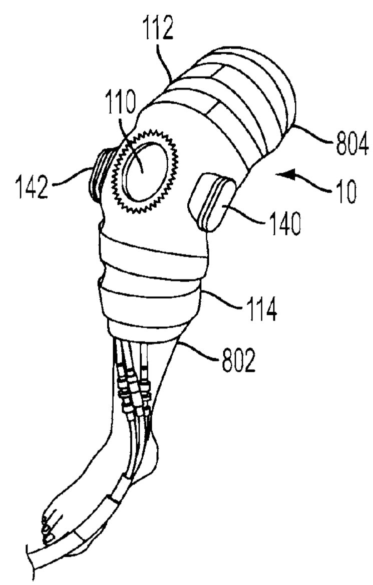
FIG. 8A is a perspective view of a expandable orthopedic device placed on a user's leg and incorporating a thermal therapy wrap.

FIG. 8A is a perspective view of a expandable orthopedic device 10 incorporating a thermal therapy wrap 106 placed on a user's leg in accordance with an embodiment. The expandable orthopedic device 10 is placed onto the user's leg such that the lower strap 114 is operable to secure a calf region 802 of the user while the upper strap 112 is operable to secure a thigh region 804 of the user. FIG. 8A further illustrates the thermal therapy wrap 106 placed on an inside surface of the expandable orthopedic device 10. In a typical embodiment, the inside surface of the expandable orthopedic device 10 may be constructed with hook and pile portions to engage the hook and pile portions 502 on a back surface 504 of the thermal therapy wrap 106. The thermal therapy wrap 106 may be adjustably positioned on the inside surface of the expandable orthopedic device 10 may be used to reduce recover time, limit edema, and protect the knees from improper movement while healing from orthopedic surgeries by having temperature control capabilities and compression capabilities. In a typical embodiment, the thermal therapy wrap 106 incorporated within the expandable orthopedic device 10 provides hot and/or cold therapy for faster relief. Furthermore, the combination of the thermal therapy wrap 106 and the expandable orthopedic device 10 is operable to, for example, accelerate post surgery healing, post workout fatigue, treat swelling, treat inflammation, treat sprains, treat joint and muscle pain, treat muscle spasms, and treat any other related injuries.

Figure 8B:
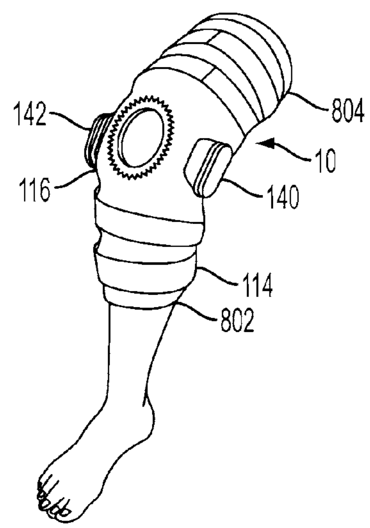
FIG. 8B is a perspective view of a expandable orthopedic device placed on a user's leg to provide joint stabilization.

FIG. 8B is a perspective view of a expandable orthopedic device 10 incorporating a buttress 116 placed on a user's leg in accordance with an embodiment. The expandable orthopedic device 10 is placed onto the user's leg such that the lower strap 114 is operable to secure a calf region 802 of the user while the upper strap 112 is operable to secure a thigh region 804 of the user. FIG. 8B further illustrates the buttress 116 placed on an inside surface of the expandable orthopedic device 10. In a typical embodiment, the buttress 116 is operable to be placed on an inside surface of the expandable orthopedic device 10 around a location on a circumferential edge of the patella opening 128. The buttress 116 may be adjustably positioned on the inside surface of the expandable orthopedic device 10 around a location on the circumferential edge of the patella opening 128 to provide a desired pressure and properly align a user's patella. According to an exemplary embodiment, the buttress 116 can be positioned in a medial or lateral direction relative to the user's patella for knee stabilization.

Figure 9:
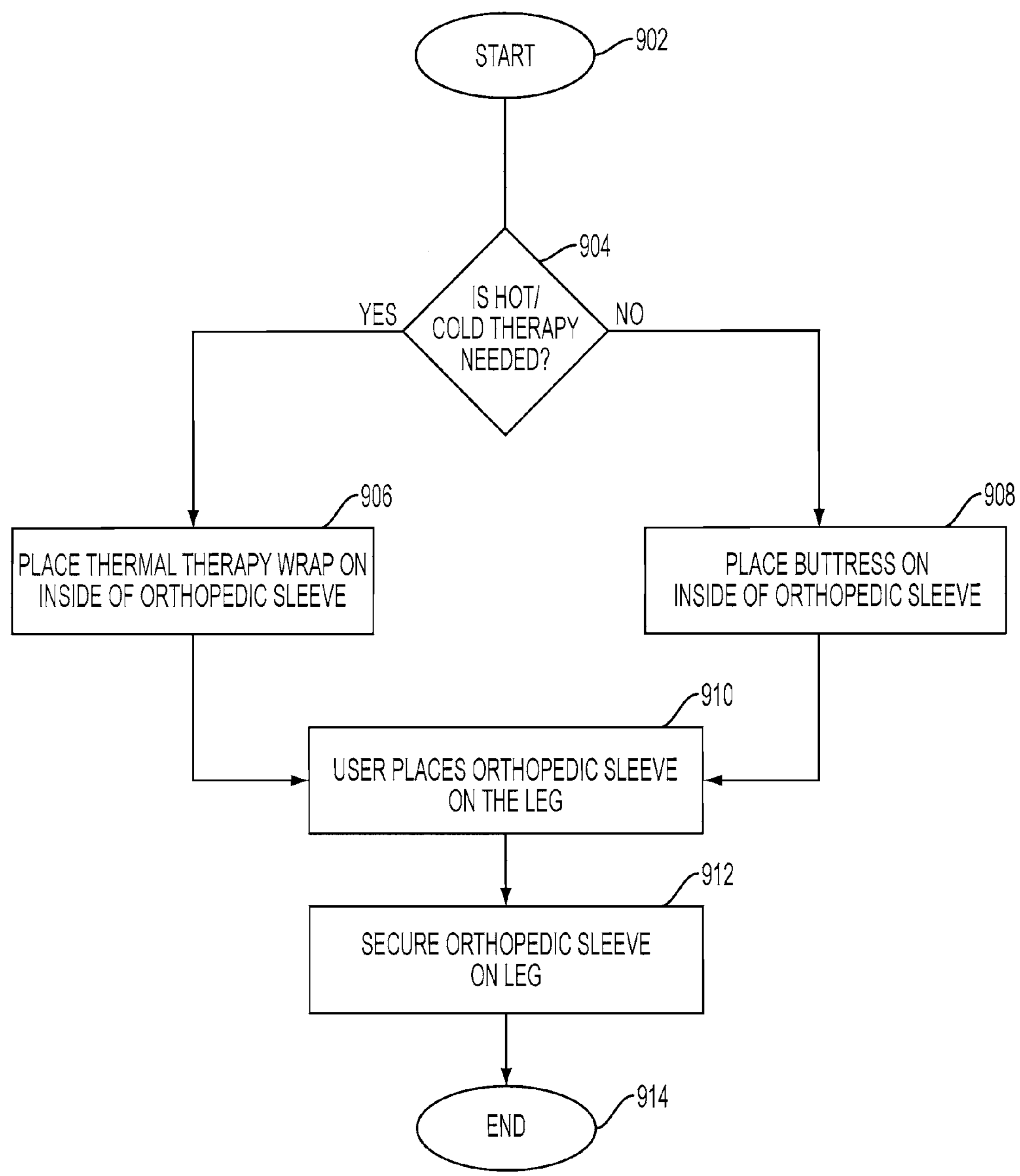
FIG. 9 illustrates a flow diagram of a method for using a therapy system.

Referring now to FIG. 9, there is shown a flow diagram illustrating a method 900 for using an expandable orthopedic device, such as, for example, an orthopedic sleeve, in combination with the thermal therapy wrap 106 and/or the buttress 116 according to an embodiment. The process 900 starts at step 902. At step 904, it is determined if a user is required to perform hot and/or cold therapy to treat the injury. If it is determined at step 904 that the user is required to perform hot and/or cold therapy, the process 900 proceeds from step 904 to step 906. At step 906, the user places the thermal therapy wrap 106 on an inside surface of the expandable orthopedic device 10. In a typical embodiment, the inside surface of the expandable orthopedic device 10 may be constructed with hook and pile portions to engage the hook and pile portions 502 on a back surface 504 of the thermal therapy wrap 106. The thermal therapy wrap 106 may be adjustably positioned on the inside surface of the expandable orthopedic device 10 and is operable to reduce recover time, limit edema, and protect the knees from improper movement while healing from orthopedic surgeries. In a typical embodiment, the thermal therapy wrap 106 incorporated within the expandable orthopedic device 10 and provides hot and/or cold therapy resulting in faster relief. Furthermore, the combination of the thermal therapy wrap 106 and the expandable orthopedic device 10 is operable to, for example, accelerate post surgery healing, post workout fatigue, treat swelling, treat inflammation, treat sprains, treat joint and muscle pain, treat muscle spasms, and treat any other related injuries.

However, if it is determined at step 904 that the user is not required to perform hot and/or cold therapy, the process 900 proceeds from step 904 to step 908. At step 908, the user places the buttress 116 on an inside surface of the expandable orthopedic device 10 for knee stabilization. From steps 906 and 908, the process proceeds to step 910. At step 910, the user places the expandable orthopedic device 10 incorporating either the thermal therapy wrap 106 or the buttress 116 onto the user leg and more particularly the knee area. At step 912, upper and lower outer straps 112 and 114 are wrapped over upper and lower inner straps 132 and 134, respectively, and fastener portions 126 and 130 are attached thereto for securing the expandable orthopedic device 10 onto the user's leg and more particularly the knee area. For example, the upper outer strap 112 of the upper fastener assembly is secured about the thigh region of the user while the strap 114 of the lower fastener assembly is secured about the calf region of the user. At step 914, the process 900 ends.

It should be noted that the term "hook and pile fasteners" is a recognized structure to one skilled in the art and is often sold under the trademark Velcro®. It is well known that the hook and pile material engage one another. In addition, various surface designs, patterns, and colors may be used as well as various thicknesses of neoprene. Likewise, various embodiments may utilize materials other than neoprene as other materials may prove satisfactory in their use as expandable orthopedic devices. The size and shape of the expandable orthopedic device 10, the thermal therapy wrap 106, and the buttress 116 as shown herein is exemplary and other cutout shapes and clearance designs may be utilized in order to accommodate various leg sizes.

According to embodiments of the invention illustrated by FIGS. 1-9, the joint therapy and stabilization system 100 is utilized for knee therapy and stabilization; however, various embodiments are not limited to knee therapy and stabilization and may be utilized in areas of need such as, for example, a limb region of a user. The limb region may be, for example, a knee region, an ankle region, an elbow region, or the like of the user. According to alternate embodiments, when the joint therapy and stabilization system 100 is utilized for regions other than the knee region, the buttress 116 may be replaced with a support specifically designed for the particular region where the joint therapy and stabilization system 100 is applied.

Although various embodiments of the therapy and stabilization system of the present invention have been illustrated in the accompanying Drawings and described in the foregoing Detailed Description, it will be understood that the invention is not limited to the embodiments disclosed, but is capable of numerous rearrangements, modifications, and substitutions without departing from the spirit of the invention as set forth herein.

What is claimed is:

1. A method for providing orthopedic therapy, the method comprising:

providing an expandable orthopedic device having an upper fastener assembly comprising a first strap and a lower fastener assembly comprising a second strap;

attaching a thermal therapy wrap on an inside surface of the expandable orthopedic device;

wrapping the expandable orthopedic device incorporating the thermal therapy wrap around a joint region of a user and securing the expandable orthopedic device therearound;

positioning first and second joint stabilization members on opposite sides of the joint region of the user to provide joint stabilization;

providing thermal therapy to the user via the thermal therapy wrap;

removing the thermal therapy wrap from the inside surface of the expandable orthopedic device;

attaching a buttress on the inside surface of the expandable orthopedic device;

wrapping the expandable orthopedic device incorporating the buttress around the joint region of the user and securing the expandable orthopedic device therearound; and adjusting the first and second joint stabilization members to provide joint stabilization.

2. The method of claim 1, wherein the joint region comprises an ankle region.

3. The method of claim 1, wherein the joint region comprises an elbow region.

4. The method of claim 1, wherein the joint region comprises a knee region.

5. The method of claim 1, further comprising positioning the buttress on the inside surface of the expandable orthopedic device around a circumferential edge of a patella opening.

6. The method of claim 5, wherein the buttress is horseshoe like in shape.

7. The method of claim 6, further comprising positioning the buttress in a medial direction relative to the joint region.

8. The method of claim 6, further comprising positioning the buttress in a lateral direction relative to the joint region.

9. The method of claim 6, further comprising providing pressure against the joint region for proper alignment thereof.

10. The method of claim 1, wherein the first joint stabilization member and the second joint stabilization member each comprise a first portion coupled to a second portion about a point of rotation.

11. The method of claim 10, further comprising positioning the first joint stabilization member and the second joint stabilization member such that the point of rotation is aligned with a second point of rotation of the joint region.

12. The method of claim 1, further comprising adjusting the expandable orthopedic device.

13. The method of claim 1, further comprising connecting the thermal therapy wrap to a fluid pump via a plurality of fluid tubes.

14. The method of claim 1, wherein the attaching comprises engaging the thermal therapy wrap to a hook and pile fastener disposed on an inside surface of the expandable orthopedic device.

15. The method of claim 1, wherein the expandable orthopedic device circumscribes portions of the user above and below the joint region.

* * * * *